United States Patent
Webb

Patent Number: 5,300,056
Date of Patent: Apr. 5, 1994

[54] DIAPER WITH SHIRT ATTACHMENT DEVICE

[76] Inventor: Sharon C. Webb, 1846 Laramie Dr., Powell, Ohio 43065

[21] Appl. No.: 992,801

[22] Filed: Dec. 18, 1992

[51] Int. Cl.$^5$ .................. A61F 13/15; A61F 13/20
[52] U.S. Cl. .................. 604/389; 604/385.1; 604/387
[58] Field of Search ............ 604/385.1, 387, 388, 604/389, 399, 401

[56] References Cited

U.S. PATENT DOCUMENTS

| | | | |
|---|---|---|---|
| 2,333,996 | 11/1943 | Gesund | 604/387 X |
| 2,366,440 | 1/1945 | Clifford | 604/388 X |
| 2,410,374 | 10/1946 | Wiese et al. | 604/388 |
| 2,578,769 | 12/1951 | Wurster | 604/401 X |
| 2,599,355 | 6/1952 | Stepp | 604/401 X |
| 2,652,057 | 9/1953 | Siegel et al. | 604/401 X |
| 3,023,752 | 3/1962 | Winn | 604/401 X |
| 4,596,569 | 6/1986 | Campbell | 604/387 |
| 4,846,815 | 7/1989 | Scripps | 604/391 |

*Primary Examiner*—Randall L. Green
*Assistant Examiner*—Elizabeth M. Burke
*Attorney, Agent, or Firm*—Thomas S. Baker, Jr.

[57] ABSTRACT

A disposable diaper has a pressure sensitive adhesive surface formed on the outer surface thereof adapted to engage the inside surface of an infant's outer body garment to thereby secure the garment to the diaper such that it overlies and protects the infant's midsection.

3 Claims, 1 Drawing Sheet ue material. A securement means secures the first layer of absorptive material to the inner surface of the second layer of moisture proof material. The diaper has an attachment means on at least one of the ends thereof for joining the two ends when the diaper is worn by an infant. At least one pressure sensitive adhesive surface is attached to the outer surface of the second layer at one end of the diaper. The pressure sensitive adhesive surface is adapted to stick to the inside surface of the outer body garment of an infant. The pressure sensitive adhesive surface faces away from the second layer of material.

DIAPER WITH SHIRT ATTACHMENT DEVICE

BACKGROUND OF THE INVENTION

The instant invention addresses the problem of keeping an infant's upper body garment such as a shirt or undershirt tucked in around the waist and diaper area to ensure that the midsection of its body remains fully covered. The objectives to be achieved by covering this area are various, including the provision of warmth, comfort, a neat appearance, and protection of the skin. As a baby becomes more mobile, moving beyond the infant stage in his/her growth, it becomes increasingly important to cover its midsection in order to protect the skin. A baby crawling on a floor inside a residence or care facility encounters rough surfaces which may scratch or otherwise harm its unprotected skin. While playing in an outside setting, covering the skin is necessary in order to protect it from the adverse effects of the sun's rays, from unsafe or unclean play areas and from the sting or bite of insects.

Because infants wear diapers for sanitary reasons any shirt or upper body garment worn by the infant cannot be tucked inside of the diaper to be held in place by the means holding the upper portion of the diaper together. If an undershirt or upper body garment is tucked inside of a diaper, when the diaper becomes wet the undershirt or outer body garment acts as a wick such that the undershirt or outer garment becomes wet which is highly undesirable.

U.S. Pat. No. 4,596,569 to Campbell discloses a shirt or upper body garment hold down device utilizing a set of four garters. The device has a central elongated elastic unit with garters at each corner which fits between the legs of an infant over its diaper. This unit adds to the bulk of an infant's clothing. Additionally, it increases the time and level of difficulty involved in changing an infant's diaper.

U.S. Pat. No. 3,559,648 to Mason describes a diaper designed to provide maximum absorptive capacity in both male and female babies. The diaper attempts to address the problem of securing undershirts or upper body garments by providing pressure sensitive tapes attached to the diaper to extend from the central portion of one or both of the edges for attachment to the lower edge of an undershirt or similar clothing worn by an infant. Additionally, the patent specification states that the diaper may be secured on the infant by pinning in a conventional manner. This design requires that the undershirt o upper body garment be tucked inside of the diaper so that the adhesive which is on the adhesive tab may engage the outer surface of the undershirt or outer body garment. Of course with this design the undershirt or upper body garment may function as a wick when the diaper becomes wet.

Accordingly, it becomes desirable to provide a diaper having an outer garment attachment means which attaches to the inside surface of the outer garment such that the garment does not have to be tucked inside of the diaper.

SUMMARY OF THE INVENTION

A disposable diaper has two sides and two ends with a central section between the two ends adapted to cover the crotch area of an infant. The diaper includes a first layer of absorptive material and a thin, flexible, second layer of moisture proof material having an outer surface and an inner surface which overlies a layer of absorptive material. A securement means secures the first layer of absorptive material to the inner surface of the second layer of moisture proof material. The diaper has an attachment means on at least one of the ends thereof for joining the two ends when the diaper is worn by an infant. At least one pressure sensitive adhesive surface is attached to the outer surface of the second layer at one end of the diaper. The pressure sensitive adhesive surface is adapted to stick to the inside surface of the outer body garment of an infant. The pressure sensitive adhesive surface faces away from the second layer of material.

DESCRIPTION OF THE PREFERRED EMBODIMENT

Figure 1:
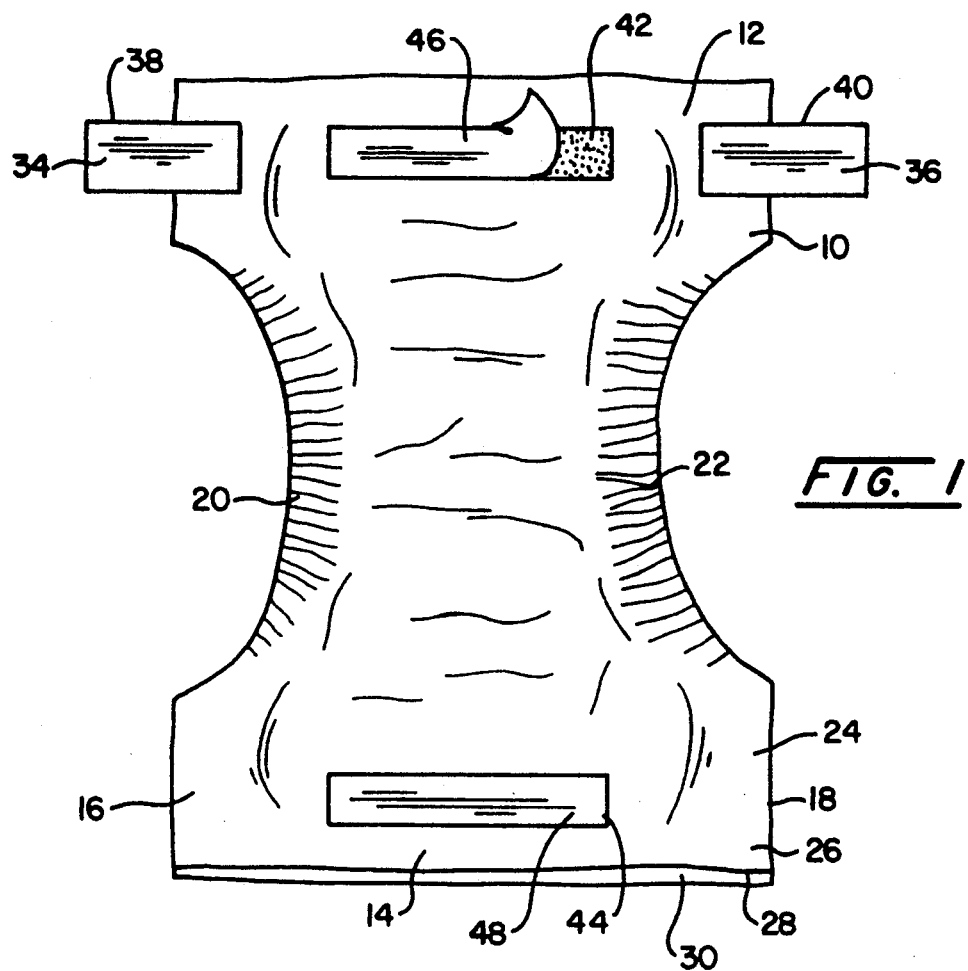
FIG. 1 is a plan view of the outer surface of a diaper.
Figure 2:
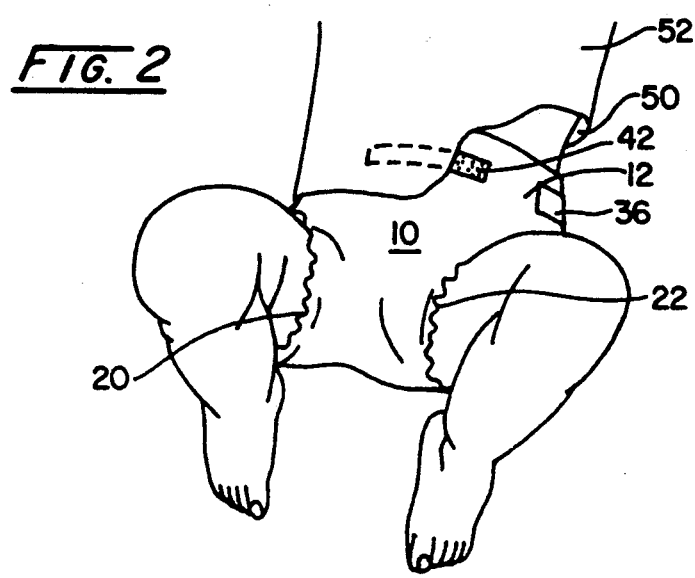
FIG. 2 is a perspective view of the diaper of the present invention illustrating the upper body garment securement means attached to the diaper.

Turning to FIGS. 1 and 2 of the drawings, it may be observed that a diaper (10) has a pair of ends (12 and 14) joined by a pair of sides (16 and 18). The sides (16 and 18) have central concave arcuate cutout portions (20 and 22) respectively which are gathered and are adapted to overlie the crotch area of an infant and fit between the infant's legs as seen in FIG. 2.

Turning again to FIG. 1, it may be observed that diaper (10) has a thin, flexible outer layer of moisture proof material (24) having an outer surface (26) and an inner surface (28). The diaper (10) also has an inner layer of absorptive material (30) which is adhesively bonded to the inner surface (28) of outer layer (24).

A pair of laterally extending fastening tabs (34 and 36) extend laterally from the sides (16 and 18) respectively adjacent one end (12) of the diaper (10). The inner surfaces (38 and 40) of the tabs (34 and 36) respectively are coated with an adhesive and are adapted to engage the outer surface (26) of the moisture proof outer layer (24) adjacent the opposite end (14) to secure the diaper (10) to an infant as depicted in FIG. 2.

Turning again to FIG. 1, a pair of laterally extending adhesive surface strips (42 and 44) are formed at each end (12 and 14) respectively of diaper (10) by applying a strip of adhesive to the outer surface (26) of outer layer (24). Strips of non-adhesive protective material (46 and 48) overlie each of the adhesive surfaces (42 and 44).

The adhesive surface strips (42 and 44) are pressure sensitive and are adapted to engage the inner surface (50) of a child's undershirt or upper body garment (52) as depicted in FIG. 2. Of course, the non-adhesive protective material (46 and 48) must be removed from the adhesive surface strips (42 and 44) prior to being brought into engagement with the inner surface (50) of the upper body garment (52). One of the adhesive surface strips (42 and 44) is adapted to engage the inner surface of the front of an upper body garment (52) whereas the opposite adhesive surface strip (42 and 44) preferably engages the inner surface (50) of the back of the upper body garment (52). Of course in those instances where anchoring of the upper body garment is unnecessary the protective materials (46 and 48) are left in place and the adhesive surfaces (42 and 44) remain covered.

The adhesive surface strips (42 and 44) may be of any desired width or length and may be positioned anywhere on the outer surface (26) of the outer surface (26) of diaper (10). Although the adhesive surface strips (42 and 44) are illustrated as engaging the front and rear inside surface (50) of an upper body garment (52), the strips (42 and 44) could be moved to the sides of the diaper adjacent the fastening tabs (34 and 36) to engage the sides of the inner surface (50) of the upper body garment (52). Also, the adhesive surface strips (42 and 44) could extend along the entire width of the diaper ends (12 and 14) to completely encircle the waist of the infant and to thereby engage a continuous circumferential strip of the inside surface (50) of the upper body garment (52).

From the above, it may be observed that because the adhesive surface strips (42 and 44) engage the inner surface (50) of an infant's upper body garment (52), the garment (52) is not tucked into the diaper (10) between the diaper and the infant's skin where it would become wet when the diaper was wet. It should be noted that the simple inexpensive adhesive strips (42 and 44) are adequate to anchor an upper body garment inasmuch as the adhesive needs to be effective only during the life of the diaper which typically is in the range of two to eight hours.

It should be noted that some diapers such as bathroom training diapers do not have fastening tabs but have the ends joined during manufacturing to form a unitary one piece ready to wear undergarment. The adhesive surface strips of the present invention would be suitable for this type of diaper.

Since certain changes may be made in the above-described system and apparatus without departing from the scope of the invention herein and above, it is intended that all matter contained in the description o shown in the accompanying drawings shall be interpreted as illustrative and not in a limiting sense.

We claim:

1. A disposable diaper having two sides and two ends with a central section between the two ends configured to cover the crotch area of an infant which comprises:
    a first layer of absorptive material;
    a thin, flexible second layer of moisture proof material having an outer surface and an inner surface which overlies said first layer;
    securement means for securing said first layer of absorptive material to said inner surface of said second layer of moisture proof material;
    attachment means comprising a single pressure sensitive adhesive engagement surface attached to said outer surface of said second layer at one end of said diaper;
    wherein said adhesive engagement surface will adhesively engage an inside surface of an upper body garment worn by said infant;
    wherein said adhesive engagement surface is the sole means of engagement with said garment; and
    wherein said pressure sensitive adhesive surface faces away from said second layer of material.

2. The diaper of claim 1 further comprising a layer of removable non-adhesive protective material which engages said adhesive engagement surface.

3. A disposable diaper having two sides and two ends with a central section between the two ends configured to cover the crotch area of an infant which comprises:
    a first layer of absorptive material;
    a thin, flexible second layer of moisture proof material having an outer surface and an inner surface which overlies said first layer;
    securement means for securing said first layer of absorptive material to said inner surface of said second layer of moisture proof material;
    attachments means comprising first and second pressure sensitive adhesive engagement surfaces attached to said outer surface of said second layer at each end of said diaper;
    wherein said first and second adhesive engagement surfaces will adhesively engage an inside surface of an upper body garment worn by said infant;
    wherein said first and second adhesive engagement surfaces are the sole means of engagement with said garment; and
    wherein said first and second pressure sensitive adhesive surfaces face away from said second layer of material.

* * * * *